(12) United States Patent
Gartenberg et al.

(10) Patent No.: US 11,950,910 B2
(45) Date of Patent: Apr. 9, 2024

(54) VALENCE STATE MEMORY ASSOCIATION

(71) Applicant: ProActive Life Inc., New York, NY (US)

(72) Inventors: Daniel Gartenberg, New York, NY (US); Daniel Micah Roberts, Washington, DC (US); Ram Nick Talwar, Sammamish, WA (US)

(73) Assignee: Proactive Life Inc., New York, NY (US)

( * ) Notice: Subject to any disclaimer, the term of this patent is extended or adjusted under 35 U.S.C. 154(b) by 665 days.

(21) Appl. No.: 16/504,285

(22) Filed: Jul. 7, 2019

(65) Prior Publication Data

US 2021/0000402 A1   Jan. 7, 2021

(51) Int. Cl.
*A61B 5/16* (2006.01)
*A61B 5/00* (2006.01)
*A61B 5/0205* (2006.01)
*A61B 5/024* (2006.01)
*G06F 3/01* (2006.01)
*G06F 1/16* (2006.01)

(52) U.S. Cl.
CPC ............ *A61B 5/165* (2013.01); *A61B 5/0205* (2013.01); *A61B 5/02438* (2013.01); *A61B 5/4812* (2013.01); *G06F 3/015* (2013.01); *G06F 1/163* (2013.01); *G06F 2203/011* (2013.01)

(58) Field of Classification Search
CPC ... A61B 5/165; A61B 5/0205; A61B 5/02438; A61B 5/4812; A61B 5/4836; A61B 5/4806; A61B 5/024; A61B 5/6891; G06F 3/015; G06F 1/163; G06F 2203/011
See application file for complete search history.

(56) References Cited

U.S. PATENT DOCUMENTS 5,123,425 A    6/1992  Shannon, Jr. et al.
5,385,144 A    1/1995  Yamanishi et al.
(Continued)

OTHER PUBLICATIONS

International search report and written opinion for PCT Application No. PCT/US21/59978 dated Feb. 4, 2022.
(Continued)

*Primary Examiner* — Ryan W Sherwin
(74) *Attorney, Agent, or Firm* — Downs IP Law LLC; Michael Downs

(57) ABSTRACT

Valence states comprise physical states associated with emotional reaction to one or more events. Users may want to alter their reaction during such valence states (improve performance, reduce stress or anxiety, etc.). Physiological responses of a user wearing a valence state monitor may be recorded during waking life. When a physiological response associated with a valence state is determined, the valence state monitor may produce one or more cues comprising sounds, lights, haptic feedback, and/or electric shock, etc. During sleep, physiological responses of the may be used to determine the user is entering a dream phase (REM or N2) and, during such periods the cue and/or additional cues may be administered such that the user's memory is triggered to prime an associative thought of the valence experience while dreaming. By priming an associative thought during sleep, the user may better work through and adapt to various valence experiences while awake.

21 Claims, 7 Drawing Sheets

(56) References Cited

U.S. PATENT DOCUMENTS

| | | | |
|---|---|---|---|
| 5,769,084 | A | 6/1998 | Katz et al. |
| 6,811,538 | B2 | 11/2004 | Westbrook et al. |
| 7,469,697 | B2 | 12/2008 | Lee et al. |
| 7,578,793 | B2 | 8/2009 | Todros et al. |
| 7,690,378 | B1 | 4/2010 | Turcott |
| 7,996,076 | B2 | 8/2011 | Burns et al. |
| 8,308,661 | B2 | 11/2012 | Miesel et al. |
| 8,378,832 | B2 | 2/2013 | Cassidy |
| 8,428,726 | B2 | 4/2013 | Ignagni et al. |
| 8,468,115 | B2 | 6/2013 | Gartenberg |
| 10,357,199 | B2 * | 7/2019 | Nachman ............ A61B 5/4815 |
| 10,463,271 | B2 * | 11/2019 | Intrator ............... A61B 5/165 |
| 10,524,661 | B2 | 1/2020 | Gartenberg et al. |
| 10,945,659 | B1 | 3/2021 | Kahn et al. |
| 11,089,993 | B2 * | 8/2021 | Kanegae ............ A61B 5/02405 |
| 11,284,834 | B1 * | 3/2022 | Milbert ............... G16H 40/63 |
| 11,311,232 | B2 * | 4/2022 | Arrington ............ A61M 21/02 |
| 2004/0122790 | A1 | 6/2004 | Walker et al. |
| 2005/0283055 | A1 | 12/2005 | Shirai et al. |
| 2006/0293608 | A1 | 12/2006 | Rothman et al. |
| 2007/0016095 | A1 | 1/2007 | Low et al. |
| 2007/0276244 | A1 | 11/2007 | Sui |
| 2009/0207028 | A1 | 8/2009 | Kubey et al. |
| 2010/0152546 | A1 | 6/2010 | Behan et al. |
| 2011/0230790 | A1 | 9/2011 | Kozlov |
| 2012/0179061 | A1 | 7/2012 | Ramanan et al. |
| 2013/0234823 | A1 | 9/2013 | Kahn et al. |
| 2014/0057232 | A1 * | 2/2014 | Wetmore ............ G09B 19/00 600/28 |
| 2014/0247151 | A1 | 9/2014 | Proud et al. |
| 2014/0269224 | A1 | 9/2014 | Huh et al. |
| 2015/0128353 | A1 | 5/2015 | Kildey |
| 2015/0208986 | A1 * | 7/2015 | Gottesman ............ A61B 5/486 600/301 |
| 2016/0015315 | A1 | 1/2016 | Auphan et al. |
| 2016/0082222 | A1 | 3/2016 | Molina et al. |
| 2017/0007480 | A1 | 1/2017 | Koch |
| 2017/0223482 | A1 | 8/2017 | Park et al. |
| 2017/0312476 | A1 | 11/2017 | Woo |
| 2019/0103034 | A1 * | 4/2019 | Walter ............... A61B 5/389 |
| 2020/0009349 | A1 | 1/2020 | Shouldice et al. |
| 2020/0100679 | A1 | 4/2020 | Gartenberg et al. |

OTHER PUBLICATIONS

Marshall L., Helgadottir H., Molle M., and Born J. (2006) Boosting slow oscillations during sleep potentiates memory. Nature 444, 610-613.

Marshall L., Molle M., Hallschmid M., and Born J. (2004) Transcranial direct current stimulation during sleep improves declarative memory. J. Neurosci. 24, 9985-9992.

Ngo H.V., Claussen J.C., Born J., and Molle M. (2013) Induction of slow oscillations by rhythmic acoustic stimulation. J. Sleep Res. 22, 22-31.

Ngo H.V., Martinetz T., Born J., and Molle M. (2013) Auditory closed-loop stimulation of the sleep slow oscillation enhances memory. Neuron 78, 545-553.

Tononi G., Riedner B.A., Hulse B.K., Ferrarelli F., and Sarasso S. (2010) Enhancing sleep slow waves with natural stimuli. MedicaMundi 54, 73-79.

Non-Final Office Action for U.S. Appl. No. 16/950,987 dated Jul. 18, 2023.

Final Office Action for U.S. Appl. No. 12/795,283 dated Feb. 5, 2013.

Final Office Action for U.S. Appl. No. 14/302,482 dated Dec. 18, 2018.

Final Office Action for U.S. Appl. No. 14/302,482 dated Dec. Jul. 31, 2017.

Non-Final Office Action for U.S. Appl. No. 12/795,283 dated Aug. 27, 2012.

Non-Final Office Action for U.S. Appl. No. 14/302,482 dated Apr. 20, 2018.

Non-Final Office Action for U.S. Appl. No. 14/302,482 dated Dec. 12, 2016.

Non-Final Office Action for U.S. Appl. No. 16/699,568 dated Apr. 10, 2022.

Notice of Allowance for U.S. Appl. No. 12/795,283 dated Apr. 14, 2013.

Notice of Allowance for U.S. Appl. No. 14/302,482 dated Sep. 30, 2019.

Final Office Action for U.S. Appl. No. 16/950,987 dated Feb. 1, 2024.

* cited by examiner

VALENCE STATE MEMORY ASSOCIATION

BACKGROUND OF THE INVENTION

Individuals sometimes encounter situations which trigger a particular emotional response, such as during episodes of drug addiction, post-traumatic stress disorder, obsessive compulsive disorder, or the like. These can also include happy associations, such as a first kiss or a visualization of your loved one telling you comforting words. In other examples, a person may want to improve performance, e.g., with respect to a particular task, losing weight, etc. Such emotional experiences may be referred to as valence experiences or valence states. In general, long periods of psychotherapy, coaching, and personal development sessions are used to alter an individual's response to such valence experiences in order to reduce a level of stress and/or anxiety, to allow the individual to improve performance of a task, or otherwise improve some aspect of the person's life.

BRIEF DESCRIPTION OF THE DRAWINGS

A left-most element numbers presented in the figures generally corresponds to the figure with which is first described. In those instances in which an element number is found in multiple figures, such an element may be the same (or similar) throughout the examples described with respect to the figures, though not necessarily.

DETAILED DESCRIPTION OF THE INVENTION

Figure 1:
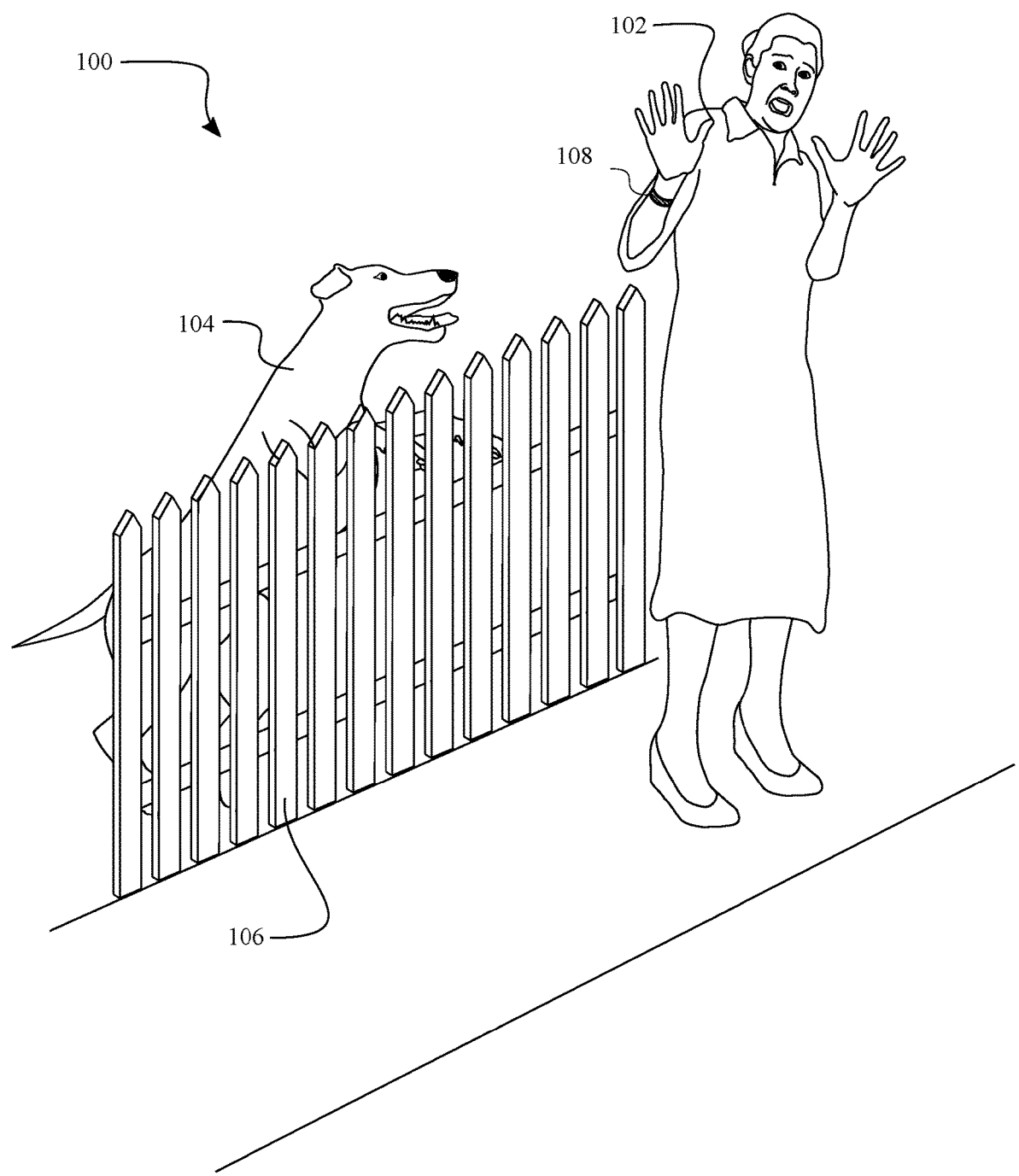
FIG. 1 represents an example of a woman experiencing a valence state of fear associated with encountering a scary dog.

As described above, it is generally difficult to alter a person's response to a valence experience. The following detailed discussion describes techniques (methods, systems, etc.) for altering and/or augmenting a person's valence experience such as, but not limited to, aiding persons in reaching achievements, such as improved cognitive function, improved skill learning, overcoming emotional states (such as anger, grief, etc.), overcoming more serious disorders (such as post-traumatic stress disorder, obsessive compulsive disorders, drug addictions, etc.), and the like by the use of creating an association with a trigger during waking-life and causing the trigger to be activated during certain stages of sleep. By causing such triggers to be activated during these certain periods, positive associations and stronger memory associations may be formed in the mind.

As a non-limiting example, a person may want to alter mental and/or physiological responses associated with a valence state (e.g., improve cognitive recall or function in order to perform a task better, reduce stress and anxiety in certain situations, reduce PTSD triggers, OCD triggers, eliminate a drug addiction, or the like). In such an example, one or more sensors on a valence state monitor worn by the user may record a physiological state of the user while awake and during a period of time associated with a valence state. A valence state may be an emotional experience involving an experience or a cognitive state associated with a task to be learned. The valence state may be, for example, a period of emotional distress, an episode of PTSD, a period of intense study or training, or the like.

Such sensors may comprise heart rate sensors, including but not limited to electrocardiography (ECG) or photoplethysmography (PPG), hydration sensors, electroencephaloghy (EEG), electro-oculogram (EOG), electrodermal activity (EDA) (which may comprise electrodermal activities), Inertial Motion Units (IMUs), actigraphy sensors, blood pressure sensors, temperature sensors, EKGs, image sensors, and the like. In some examples, more complex techniques can be used to augment detection of an emotional state. As a non-limiting example, image data from a camera (and/or additional sensor data) may be used in conjunction with facial recognition techniques (and/or other sensor data) in order to classify an emotional state of the associated user (happy, sad, distressed, angry, etc.). In some examples, the user may trigger recording of the event by interacting with a device, such as by pressing a button. In some examples, the triggering event associated with the physiological states may comprise a machine learned model which is trained based on previous associations of the user and the state associated with the valence experience.

Once in the state, a Pavlovian cue (or simply a cue, as used herein) may be triggered. Such a Pavlovian cue may be, for example, and one or more of audio sounds (including prerecorded words and/or phrases recorded by the user or a friend/loved one, which in some cases may comprise a mantra to be repeated by the user in waking life), sounds recorded by a microphone recorded during the valence state, music, visual signals (individual points of light, such as LEDs, images as may be displayed on a screen, etc.), haptic transducers, olfactory triggers (smells), electrical discharges (shocks), or any combination and/or sequence thereof. In at least some examples, the Pavlovian cue may be determined by a psychotherapist in accordance with a treatment regimen or otherwise determined based on the treatment and/or valence state and may vary from time to time. In some examples, the cue may be recorded by the individual, a friend or loved one, or otherwise associated with a mantra associated by the individual in waking life. In some examples, the cue may be a reminder, such as, for example, a reminder for the user to question whether they are currently dreaming, which may otherwise help induce a lucid dreaming state.

In various examples, the sensors and/or additional sensors may determine when a user is asleep and, if so, in which stage of sleep the user is. The additional sensors may comprise, for example, actigraphy data (IMU, heart rate, body temperature, etc.), ECG, EEG, polysomnography, microphones, blood pressure sensors, and the like. Such sensor data may be used to determine a stage of sleep in accordance with the techniques described in the U.S. patent application Ser. No. 14/302,482 entitled "Sleep Monitoring and Simulation" filed on Jun. 12, 2014, the entire contents of which are incorporated herein. In at least some examples, a device may determine which stage of sleep a user is in and, when in a dream state (e.g., N2 or REM), play the cue. In some examples, an EEG and/or EOG may be used in conjunction with other sensors (heartrate, IMU, body temperatures, etc.) during a first session in order to associate (e.g. correlate or otherwise determine) which periods of sleep correspond with the other sensors such that further dream states can be determined by the other sensors alone. In at least some of these examples, having an electrode by an eye of a user may be important for measuring a dream state of sleep of the user. An intensity of the cue may be based on a previous physiological response recorded during the wakeful valence experience and, in some examples, gradually increased. In at least some examples, the intensity (or level) of the cue may be so as to create a micro-arousal, otherwise known as a cortical arousal, but not meet or exceed a threshold level which would bring the user out of the state, otherwise known as an arousal threshold. Such cortical arousals may be brief disruptions of sleep that do not rise to the level of consciousness in the sleeper (i.e., the person experiencing the cortical arousal has no recollection of the event). Often, cortical arousals are associated with sleep apnea and periodic limb movement disorder, but can also occur in healthy sleepers.

In some examples, a psychotherapist may, based on the one or more cues and associations, alter or otherwise adjust the stage of sleep the cues are triggered and/or adjust the cues themselves (levels and/or combinations of audio, visual, olfactory, haptic, etc.). In any such example, however, such cues may be played below an arousal threshold such that the user does not move into another phase of sleep. Such arousal thresholds may be previously determined by playing a cue until arousal in previous sleep sessions and subsequently reducing an intensity (volume, brightness, etc.) by a fixed percentage below such arousal threshold. In at least some examples, the cues may be played in an order and/or in addition to other light, sound, haptic, or other output in order to guide the user into a particular sleep state (e.g., to help guide a user into a particular sleep state). In some examples, the cues may be played with an increasing intensity during sleep. In at least some examples, the cues may be decreased once an arousal threshold is met and/or adjusted during the night in order to continue to provide cues below the user's conscious awareness.

After waking up from the sleep session, a therapist may engage with the user to inquire about what was recalled from the dream state. Feedback from the user may be used to further adjust the one or more cues, or otherwise alter the treatment until a desired outcome is achieved.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding background or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The Valence Experience

FIG. 1 illustrates an example 100 in which a user 102 may want to alter their reaction during a valence experience. The user 102 may want to control their reaction in certain situations, such as, for example, overcoming a fear of dogs. As depicted in FIG. 1, user 102 may be passing through an environment where a dog 104 is present. As depicted in FIG. 1, the dog 104 may be bound by a fence 106, but be standing on the fence 106 and barking, growling, or otherwise intimidating the user 102. In such a state, the user 102 may experience a valence experience, or otherwise be referred to as being in a valence state. That is to say that the user 102 is in a state associated with an emotional and/or physiological response associated with a particular situation, task to be performed, or the like. In FIG. 1, the user 102 may have an elevated heart rate, increased electrodermal activity due to sweating/perspiration, increased respiration, and the like.

Though not depicted, virtual, mixed, and/or augmented reality may be used to simulate such a valence state while the user is wearing the valence state monitor 108 during interaction with a psychotherapist. In such examples, the psychotherapist may alter, in real time (and/or based on instantaneously recorded data from the valence state monitor 108) one or more cues for the user in adapting to the valence state.

In at least some examples, the user 102 may be wearing a valence state monitor 108. As depicted in FIG. 1 for illustrative purposes, such a valence state monitor 108 may be in the form of a wrist watch, or other wrist worn device. However, any other form of the device is contemplated, such as, but not limited to, ankle-worn devices, patches to be worn on portions of the body, non-invasive devices which can perform physiological measurements, etc. Additional details of such a device is described in detail below with respect to FIG. 2. For the purposes of discussion with respect to FIG. 1, the valence state monitor 108 may be continuously monitoring various physiological parameters of the user 102, such as, but not limited to electrodermal activity (conductance), heart rate, respiration, blood pressure, and the like. In at least some examples, such a valence state monitor 108 may further store such measurements in a buffer of 30 seconds, 1 min, 2 min, 5 min, or the like.

In some examples, the valence state monitor 108 may be triggered by the user 102 to record at least a portion of the physiological response to the valence state. Such triggering may cause the valence state monitor 108 to record signals associated with the valence experience for a fixed period of time (e.g., 30 s, 1 min, 2 min, 5 min, etc.) and/or until such an experience has ended. In at least some examples, the ending period of the valence state may be determined based on a change in the monitored physiological response. As a non-limiting example, a heart rate of the user 102 associated with the valence state may be 120 bpm. In additional and/or alternate examples, motion detected by, for example, an IMU associated with the device may be used to determine that the individual has not engaged in physical activity that would otherwise be associated with such an elevated heart rate in order to determine that the individual is likely experiencing a valence state. In such an example, the valence state monitor 108 may assume that such a valence state has ended in the event that the heartrate of the user 102 does not meet or exceed a threshold percentage of the heartrate recorded during the valence response (e.g., less than 80% of the recorded heartrate). In at least some additional and/or alternative examples, a physiological baseline may be determined from any one or more of the physiological measurement sensors when the user lies down to sleep (e.g., an average heartrate during the first 1 minute, 5 minutes, hour, etc.). In such examples, a valence state may be determined once measurements from any one or more of the physiological sensors deviate by more than a threshold from the recorded baseline. Further, an end of the valence state may be associated with a return of such physiological measurements to at or below the same or similar threshold. Of course, any one or more physiological responses (or combinations thereof) may be used to determine that the valence experience has ended.

In at least some examples, such a valence state monitor 108 may detect (i.e., without the need for the user 102 to trigger) the occurrence of a valence state. Such a detection may be based on, for example, one or more machine learned models. In such examples, the instantaneously recorded physiological parameters may be input into the one or more machine learned models of the valence state monitor 108 and the onset of a valence experience may be determined by such a model. In at least some examples, such machine learned models may be trained based at least in part on previous onsets of valence states associated with the user 102. Such previously recorded valence states may be referred to as the ground truth for training such machine learned models and may be associated with previous triggers by the user 102, patterns of anomalous physiological states (e.g., physiological states which may be clustered based on the one or more physiological parameters recorded according to one or more clustering algorithms), or the like and the one or more physiological parameters recorded during those one or more previous states.

In some examples, a valence state may be determined by the valence state monitor 108 based on one or more external triggers. Such triggers may be determined based on a recognized sound (whether audible or not), visual sequence, or some combination thereof provided by an external source. As a non-limiting example, a commercial may have particular sounds (either audible to the user 102 or not) which may be recognized by the valence monitor device 108 in order to determine that the user 102 is listening to the commercial. Such recognition of externally applied sounds, lighting sequences, or otherwise may be used as a basis for such a trigger.

Regardless of how the valence state monitor 108 is triggered, after the device is triggered (e.g., either by the user 102 or automatically), the valence state monitor 108 may produce one or more cues. As non-limiting examples, the valence state monitor 108 may play one or more sounds, music, form one or more light patterns (including images), discharge a minor electric shock, provide haptic (such as vibrational) output, or the like. In at least some examples, such sounds may comprise a voice of the user 102 and/or a friend or loved one repeating a message or mantra. The one or more stimulations, whether alone or in combination with others, may be generally referred to as a cue or Pavlovian cue throughout the disclosure.

Recorded data of the physiological sensors of the valence state monitor 108 may be stored on the valence state monitor 108 more permanently than the instantaneous recording that exists in one or more memory buffers on the device for subsequent download to a computerized system, or otherwise transmitted wired or wirelessly (e.g., over Bluetooth, WiFi, 3G, 4G, LTE, etc.) for additional processing. In at least some examples, such physiological data may further be associated with a unique ID or other data which can be used to identify the user 102. In various examples, such sensor data may also be associated with a timestamp indicative of when the valence state occurred (e.g., when the trigger started), as well as a duration of the valence experience.

Once identified, similar cues may be provided to the user 102 when in a dream state in order to aid in helping the user 102 overcome, enhance, or otherwise alter an emotional, physical, and/or cognitive response associated with the valence experience by priming an associative memory. Additional details of such is explained in detail below with any one or more of FIGS. 3A-3C, and 5-6.

Though depicted with respect to FIG. 1 for illustrative purposes as a valence state associated with fear of a dog (dog 104), the present invention is not meant to be so limiting. Similar valence states (or valence experiences) can be associated with, for example, wanting to improve a task (cognitive and/or physical performance), overcoming loss/grief, overcoming anger, inducing a lucid dream state, minimizing the effects of, for example, PTSD, OCD, etc., and the like.

The Valence State Monitor

Figure 2:
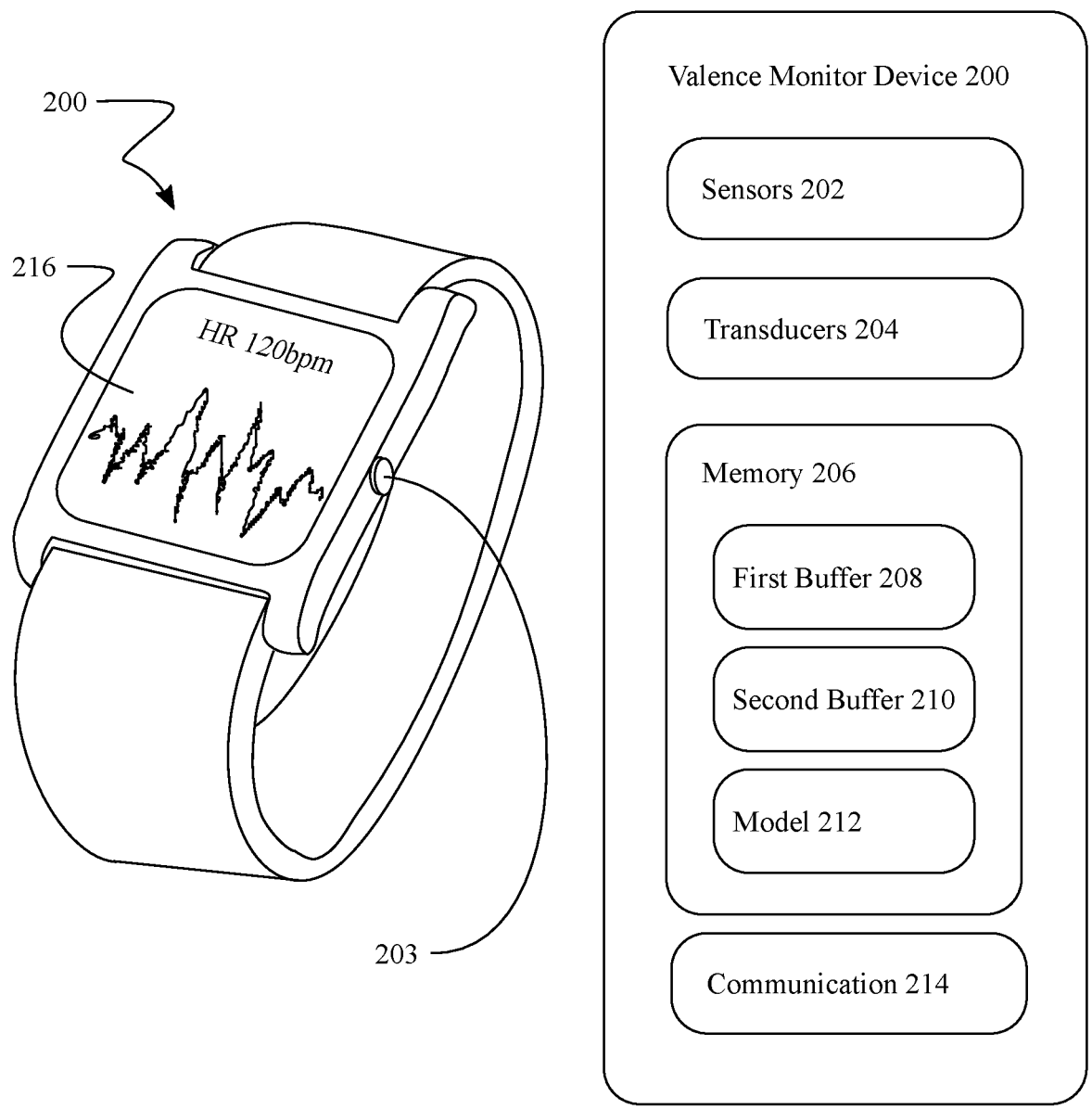
FIG. 2 is an illustration of an example valence state monitor, such as worn by the woman illustrated in FIG. 1.

FIG. 2 illustrates an example valence state monitor 200 (such as valence state monitor 108). Although depicted in FIG. 2 for illustrative purposes as a wrist-worn device (such as a watch), the invention is not meant to be so limiting. As above, such a valence state monitor 200 may be worn on an ankle, about a leg, across a chest, or any other portion which allows for recording of physiological signals. In at least some examples, such a device need not be a single device. As a non-limiting example, a wrist portion having sensors (sensors 202) may be worn and transmit data (wired or wirelessly) to a second device (e.g., a smartphone, etc.), such as over Bluetooth, NFC, WiFi, LTE, 5G, 4G, etc. The second device may then perform other operations. However, for the purposes of discussion, the wrist portion and second device together may be referred to as the valence state monitor 200.

The valence state monitor 200 may be equipped with one or more sensors 202 to monitor the physiological state of a user. The one or more sensors 202 may comprise any one or more of heartrate sensors, electrodermal activity sensors, respiration sensors, EEG sensors, ECG sensors, actigraphy sensors, blood pressure sensors, Inertial Measurement Units (IMUs) (which, in turn, may comprise one or more accelerometers, gyroscopes, magnetometers, etc.), pulse oximeters, thermometers (e.g., to measure a skin and/or body temperature), hydration sensors, microphones, and the like. In at least some examples, additional sensors (e.g., cameras) may be used to detect (or otherwise determine) an emotional state of the user. As a non-limiting example, facial feature recognition based on camera data (and/or a combination of other sensor data) may be used to determine whether the user is happy, sad, angry, depressed, etc. Such sensors may broadly be determined to be invasive and/or non-invasive.

In at least some examples, different sensor data may be emphasized (prioritized for determining a valence state) based on the task chosen by the user. As non-limiting examples, a user attempting to learn a task may have EEG data emphasized (e.g., as beta and/or gamma waves may be indicative of being in a focused state), whereas a user attempting to overcome a stressful state may have increased heartrate variability, increased electrodermal activities, higher variability in IMU measurements, and the like. In such examples, such responses may be prioritized over brainwave data in determining the user is having a valence experience.

As illustrated in FIG. 2, a screen 216 may display sensor data from any one or more of the sensors 202. As illustrated, the screen 216 is displaying the instantaneous heartrate of the wearer. Of course, any combination of sensor data provided by any one or more of the sensors 202 is contemplated.

In at least some examples the valence state monitor 200 may additionally have an input trigger 203. Such an input trigger 203 may comprise a button (physical, touch screen (capacitive, inductive, resistive), or the like), etc. In such examples, when the input trigger 203 is depressed (or otherwise activated), a trigger signal is generated. In some examples, such input trigger 203 may comprise a microphone and use natural language processing, various natural language APIs (such as Amazon's Alexa Skills Kit, Google Assistant API, etc.) such that when a given word or phrase is said by a user wearing the valence state monitor 200, the trigger signal is generated (e.g., "start", "start recording", "now", or the like). In at least some examples, the valence state monitor 200 may additionally, or alternatively, perform gesture recognition (e.g., by determining one or more gestures, such as twisting a wrist or other motion of the hand, based on, for example IMU measurements) to generation of the trigger signal. Interacting with the input trigger 203 may cause a portion of data generated from the one or more sensors 202 to be recorded more permanently, as discussed in detail below.

As described in detail above, in some examples, the valence state monitor 200 may not comprise input trigger 203 (or otherwise the input trigger 203 may not be used to generate the trigger signal). In such examples, a machine learned model 212 may be used to generate such a trigger signal, as will be described in detail below.

The valence state monitor 200 may further have one or more transducer(s) comprising light emitters (LEDs, LCD displays, OLED displays, infrared emitters, etc.), haptic and/or vibrational elements, speakers (which may include bone conductance, including bone conductance in glasses or as an eye mask when sleeping), electric shock discharge, and the like. In response to the trigger signal (e.g., received directly or indirectly), one or more transducer(s) 204 may emit a cue. Such a cue may be a combination of one or more sounds (notes, music, pre-recorded voices, etc.), lights or visual displays, haptic feedback, and/or electric shock discharges. In any one or more examples, such transducers may comprise, for example, speakers, lights (including infrared lights, such as LEDs), screens, haptic feedback devices, vibrational elements, electric shock discharge devices, and the like.

The valence state monitor 200 may comprise memory 206. Such memory 206 may be any form of memory described herein, such as described in detail with respect to FIG. 4. In at least some examples, memory 206 may comprise portions dedicated to different data storages and/or have different memories may be used for such data storage. In such examples, a first buffer 208 may be large enough to store a given amount of continuously streamed sensor data from the one or more sensor(s) 202. In those examples, sensor data may be continuously recorded in such a first buffer 208 such that a previous amount of time of recorded data is stored (e.g., past 10 seconds, past 20 seconds, past 30 seconds, etc.). In such examples, a valence state may have started before a trigger signal is generated. By constantly recording in a first buffer 208, all physiological responses from such a valence state may be preserved for analysis.

Memory 206 may further comprise a second buffer 210. In response to receiving the generated trigger signal, data stored in the first buffer 208 may be copied (or otherwise transferred) to the second buffer 210. A subsequent amount of sensor data from the one or more sensor(s) 202 may then be directed to the second buffer 210 (e.g., a next 10 s, 20 s, 30 s, etc.), or otherwise until a valence state has ended (e.g., by determining whether a physiological state has changed, in response to a changed output from the machine learned model, and the like). Further, in some examples, such data storage may be directed to both buffers continuously and substantially simultaneously. In other examples, the first and second buffers 208, 210 may comprise a single buffer. Regardless, sensor data stored in the second buffer 210 may be stored for a longer period of time than in first buffer 208 (e.g., until transmitted to a remote storage, until the next valence event, or the like).

In at least some examples, the memory 206 may further comprise an operating system, as well as non-transitory computer readable media storing instructions thereon which, when executed by one or more processors (e.g., of the valence state monitor 200, not pictured) cause the one or more processors to perform one or more operations. In such examples, the instructions may comprise a machine learned model 212. The model 212 may be trained based on previously acquired data indicative of the onset of a valence state of the user. As a non-limiting example, previous sensor data that was recorded in response to the trigger signal may be analyzed for unique patterns, features, etc. indicative of such a valence state. In at least those examples when a valence state is measured during sleep, such measurements may be regardless of the effectiveness of the corresponding cue (discussed in detail below) to elicit the intended response. In such examples, the model 212 may directly recognize the onset of such a valence state and generate the trigger signal without the need for the user to interact with the input trigger 203.

The valence state monitor 200 may further comprise a communication component 214. Such a communication component 214 may enable the valence monitor 200 to send and/or receive data to a further device, system, computer, etc. either via a wired and/or wireless connection, or any other wired or wireless communication component and/or protocol described herein. In such examples, sensor data stored in the second buffer 210 (and/or instantaneously measured) may be transmitted (and/or continuously transmitted in the case of instant sensor data) to another device for additional processing. As will be described in detail below, such sensor data may be used to determine how effective a given cue is at altering, or otherwise augmenting, the user's valence experience. In some examples, the model 212 may be trained by another device and subsequently transmitted to the valence state monitor 200 via such a communication component 214.

Sleep Training Systems

Figure 3A:
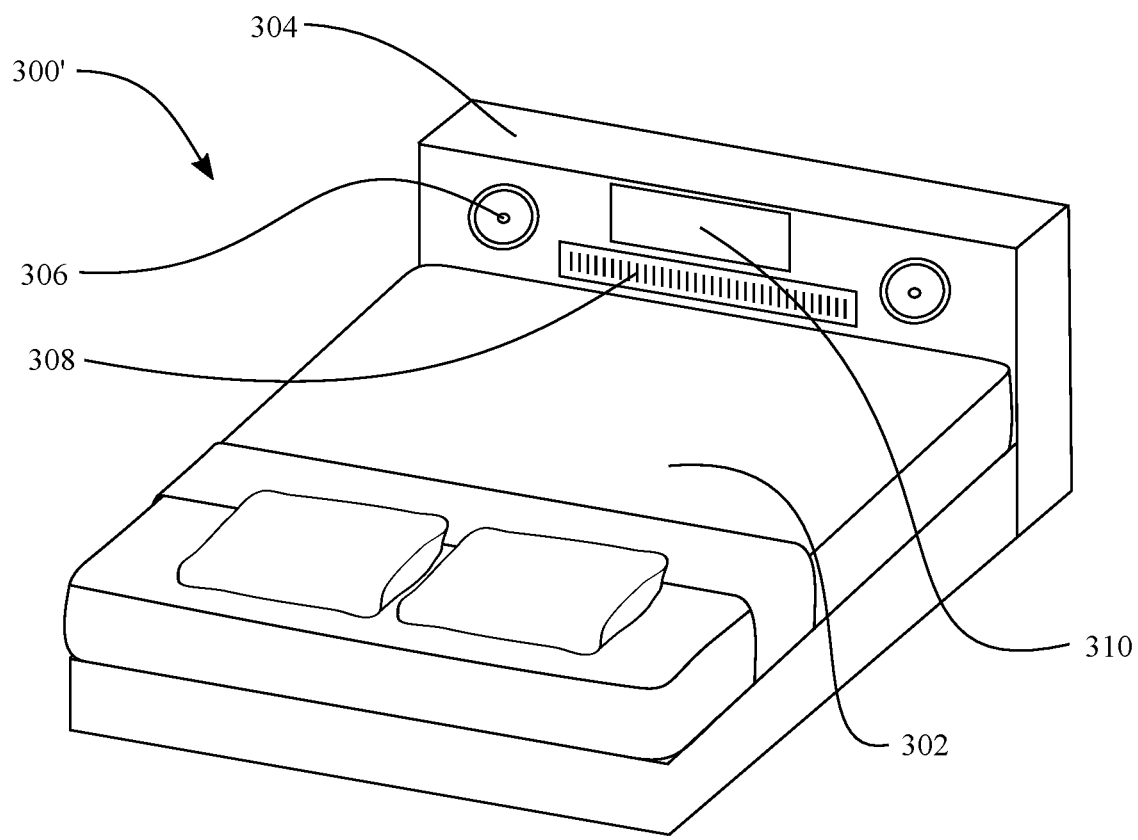
FIG. 3A is an example sleep training system in which one or more sensors and/or transducers are present on a footboard of a bed.
Figure 3B:
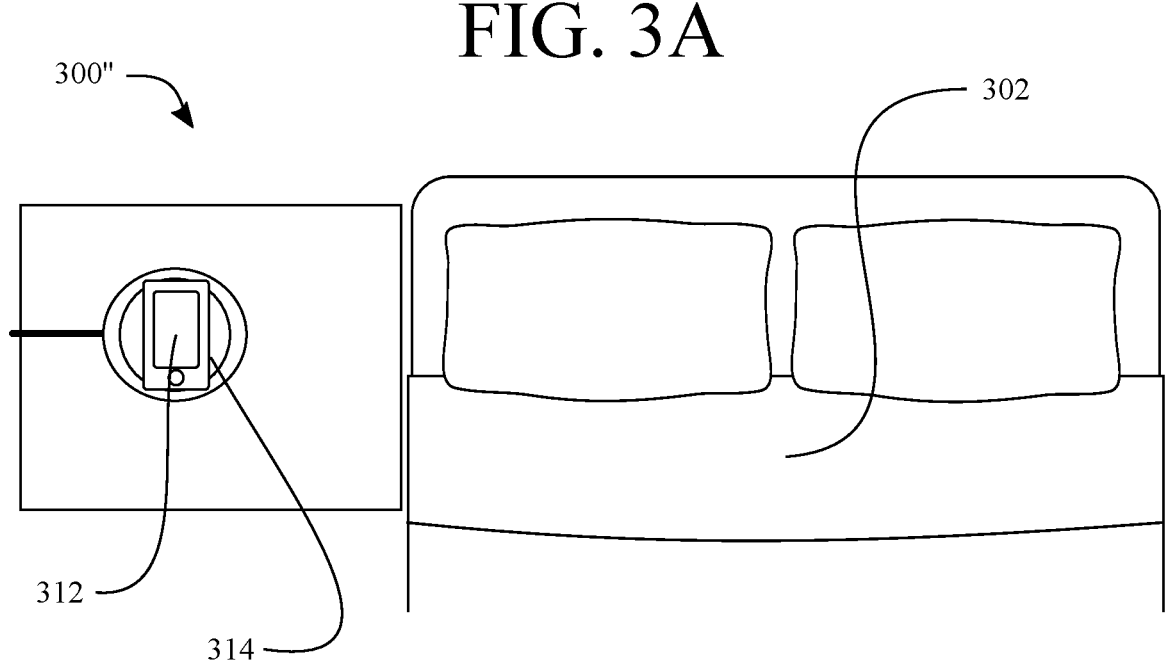
FIG. 3B is an example sleep training system in which one or more sensors and/or transducers are present in a user device and/or baseboard associated with a bed.
Figure 3C:
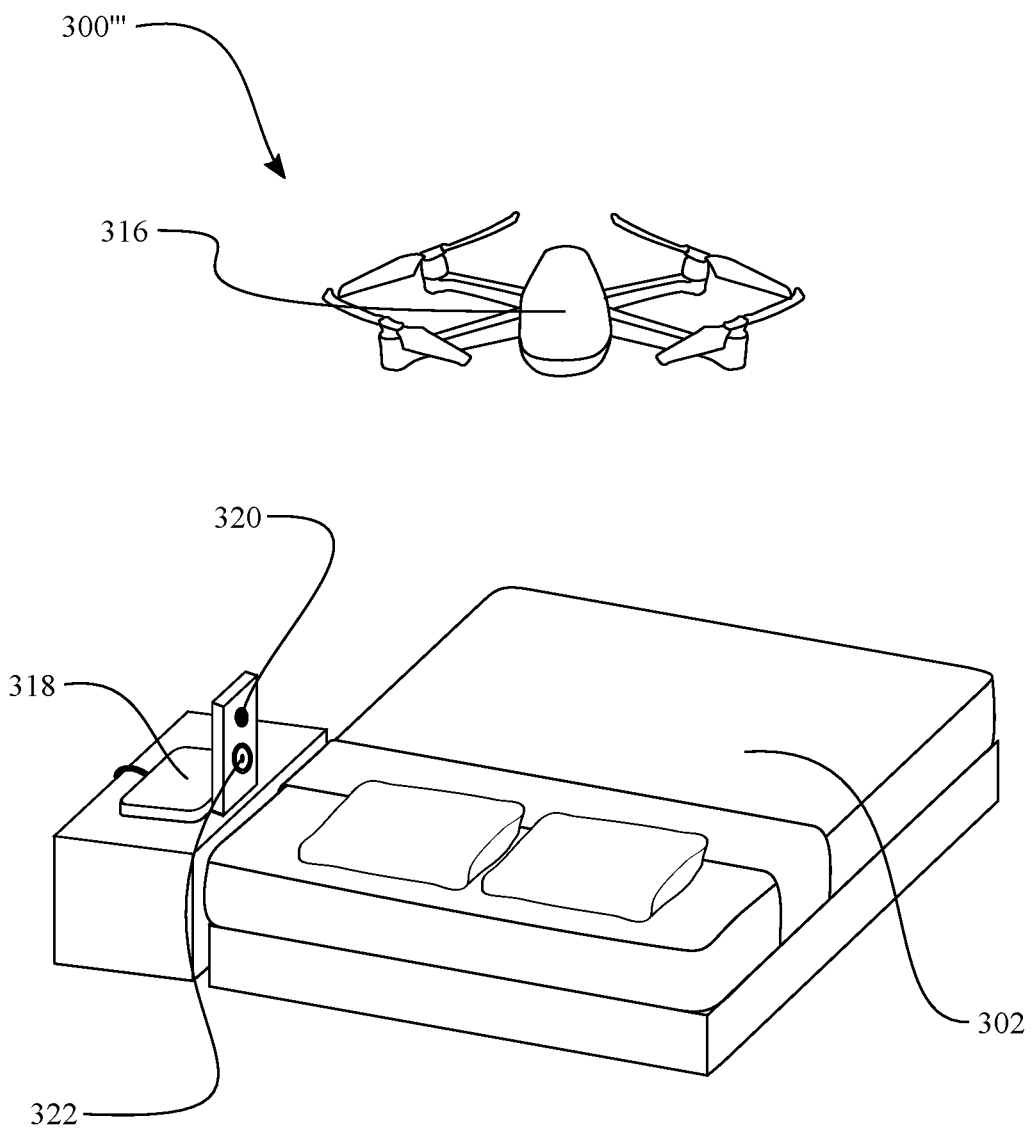
FIG. 3C is an example sleep training system in which one or more sensors and/or transducers are present on a drone.

FIGS. 3A-3C depict several examples of sleep training systems 300 in which sleep can be used to alter or improve such a valence state response. In all of the examples provided, physiological data about the user may be continuously collected when the user is asleep. In at least some examples, such data may be detected by the valence state monitor 200 worn during sleep and/or additional sensors (ECG, EEG, actigraphy data, etc.) associated with such sleep training systems 300. The sensor and/or additional sensor data may be used to determine when a user is entering a particular phase of sleep (e.g., REM or N2, though any other phase is contemplated). Sensor data used may comprise EEG data, ECG data, EOG data, polysomnography data, actigraphy data, photoplethysmography (PPG) data, heart rate data, blood pressure data, body temperature data, etc. as may be determined by one or more sensors of the valence state monitor 200 and/or the sleep training system 300. Such a determination may be made, for example, in accordance with the techniques described in U.S. patent application Ser. No. 14/302,482 referenced above, the entire contents of which are incorporated by reference herein. Upon entering such a sleep state, one or more cues (which may differ from the cue described with respect to FIG. 2) may be initiated by one or more of the valence state monitor 200 and/or the sleep training system 300.

As depicted in FIG. 3A, a sleep training system 300' may comprise a bed 302 and a footboard 304 and/or headboard (not depicted) comprising one or more transducers. The transducers may comprise, for example, speakers 306 (capable of playing sounds such as notes, music, prerecorded voices (which may be a recording of the user stating a mantra or the voice of a loved one stating a word or phrase), etc.), air conditioning/fan 308 (capable of changing a temperature of the room and, hence, the user), display and/or lighting 310 (capable of emitting light at a particular frequency (color), including infrared and/or images), as well as various other elements capable of interacting with the user while asleep. In some examples, the footboard 304 may comprise a reservoir for storing a liquid (e.g., water) which may be atomized and misted over the user and/or otherwise used to alter a level of humidity. In some examples, various other mechanisms may be used to provide an olfactory experience (e.g., triggering certain smells). As will be described in detail below, various levels (intensities of activation) associated with the cues (e.g., volumes, etc.) may be altered based on a distance the transducer is from the user and/or the desired response.

Similarly, as depicted in FIG. 3B, the sleep training system 300" may use a user's personal device 312 (e.g., smartphone, laptop, etc.) placed on a baseboard 314 next to the user's bed 302. The baseboard 314 may be used for both charging the device 312, as well as providing one or more additional sensors or transducers not otherwise available in the user's device 312. The device 312 and/or baseboard 314 may then record physiological measurements and/or initiate the various cues. In either example, the valence state monitor 200 may be worn by the user to communicate physiological data to the user regarding the sleep state of the user. In such examples, where a user device 312 is used alone to determine a sleep phase or state of the user, previously recorded EEG and/or ECG measurements may be correlated to other sensor data to provide an indication of sleep phase. In such an example, physiological responses from sensors available in the valence state monitor worn by the user and/or sensors available in the user device 312 may be correlated to a sleep phase or state previously determined using additional sensors (such as EEG and/or ECG) such that future determinations of sleep phase or state may be determined based on the subset of sensors found in the valence state monitor and/or user device 312 alone.

As shown in FIG. 3C, one or more drone(s) 316 may further be used to provide the physiological monitoring and/or initiate the various cues. Such drone(s) 316 may comprise (though not depicted for clarity) various sensors and/or transducers (such as those depicted in FIG. 3A), such as, but not limited to infrared lights, lights of visible frequencies, sonar, RADAR, fans (for providing cooling to the user), GPS, a reservoir of liquid (such as water, for misting the user or altering a humidity level), speakers, microphones, cameras, and the like. In any one or more of the examples above, the sensor data may be used to determine a dream state of the user (e.g., REM or N2) and the various transducers may be used to initiate the one or more cues. As further depicted in FIG. 3C, a drone baseboard 318 may provide wireless recharging for the drone(s) 316 such that when in proximity to the drone baseboard 318, power sources on the drone 316 may be recharged. Further, in some examples, the drone baseboard 318 may comprise additional sensors and/or transducers in order to monitor the user and/or initiate the cues. As shown here as a non-limiting example, such a drone baseboard 318 may further comprise one or more light sources 320, as well as one or more speakers 322, microphones, and the like. Of course, as above, levels associated with the various cues may be dependent on a distance of the drone(s) 316 from the user in the bed 302. A position of the user in bed may be determined based at least in part on the valence state monitor 200 worn (e.g., triangulating a wireless signal), based on one or more cameras on the drone(s) 316, and the like. In at least some examples, the drone(s) 316 may first be calibrated by first setting the drone(s) 316 at a location where the user will be sleeping. As illustrated in FIG. 3C, such a position may be on the drone baseboard 318. In such an example, the drone(s) may be calibrated so as to know an intended location to deliver the cue(s) during sleep. Additionally, or alternatively, pressure sensors (or the like, such as, but not limited to weight sensors) in the bed 302 (in addition to image sensors on the drone(s) 316), may enable the drone to locate and/or identify the user in the bed 302 for precisely delivering the cue at the prescribed level (e.g., based on relative distance as may have been determined based at least in part on the calibration procedure above).

In any one or more of the examples described herein, the user may additionally, or alternatively, wear goggles to aid in determination that the user is entering a valence state while sleeping. In at least some examples, goggles may additionally, or alternatively, include one or more accelerometers, gyroscopes, magnetometers, or other inertial measurement units, in order to determine whether the user is sleeping. Of course, any number of additional sensors (such as, but not limited to, electrodermal activity sensors) may be further utilized by the goggles in determining a sleep state. In some examples, such goggles may comprise one or more electrodes to measure an EOG to help determine that the user is dreaming. In some such examples, the goggles may further provide the one or more cues using bone conductance.

Such cues may be determined in accordance with the valence state the user is hoping to alter. As non-limiting examples, for a user trying to overcome PTSD, sounds associated with the trauma event may be played (which may be recorded, for example, by the valence state monitor during the valence state experienced); for users attempting to overcome drug abuse, the sounds of other drug user's voices with whom the user partakes may be played, a regiment of sounds/stimulations may be played including a mantra (e.g., "You love your children"); in the event of Obsessive Compulsive Disorders, a prerecorded voice of a loved one saying "It's OK, everything is OK" can be played; in the event of the woman in FIG. 1, a dog barking may be played in combination with calming sounds for the purpose of dissociating the negative, fearful, experience with something different and/or positive, etc. In at least some examples, such as those examples in which the valence state is associated with a commercial being played, the cue may comprise the same cue as played during original recording of the valence state and/or at least a portion of the commercial. By playing such cues during sleep, a user's mind may be primed for associative thought in the dream to achieve targeted memory reactivation (e.g., replaying the moment associated with the valence event which occurred during the day in a dream in which the user has more control with respect to the response). Such association may be used, for example, for immersion therapy and/or replaying an associative memory to improve task performance or otherwise shift the Pavlovian response to a stimulus.

In at least some examples, an arousal threshold may be determined. Such an arousal threshold may correspond to any one or more levels (intensities) associated with the one or more transducers in any one or more of FIGS. 3A-3C and/or the valence state monitor such that meeting or exceeding such a level may cause the user to transition to a different sleep phase (e.g., out of N2 or REM), experience a shift in heart-rate variability, and/or experience a brief awakening from sleep. In such examples, one or more sensors (e.g., of the valence state monitor 200 worn while sleeping and/or of the sleep training system 300) may continuously monitor the user for micro-arousals and continuously increase levels of the one or more cues. Such micro-arousals may be associated with, for example, a change in motion and/or heart rate variability (as may be measured by a heart rate monitor of either the valence state monitor and/or the sleep training system 300). If there is a clear change in variability (e.g., greater than or equal to a threshold variability) within a given amount of time (0.5 to 8 seconds), a sleep phase threshold may be determined. Such a threshold may indicate a level in which, when actuated by one or more of the transducers, the user remains asleep and undisturbed by the stimulation, but exceeding such thresholds would wake the user or shift the user to an unwanted phase of sleep. Such thresholds may be recorded so that the process need not be repeated from one session to the next. In such examples, the thresholds determined may be used such that cues are played at a given decibel level less than the threshold. In any such examples, cues may be played at a maximum level (e.g., the given decibel level less than the threshold) to ensure the user is processing the cues while asleep, while ensuring they do not transition to another phase of sleep or awaken from sleep. In some examples, however, it may be advantageous to play cues at a level to intentionally wake the user. As a non-limiting example, it may be safer to the user to wake them up, as opposed to having them in an uncontrolled state during sleep, such as, for example, when a user is experiencing severe night terrors. In at least some examples, one or more of the transducers (either of the valence state monitor and/or the sleep training system 300) may be used to guide the user into an ideal sleep phase (e.g., a dream state) and/or keep the user in such a state as long as possible. As a non-limiting example, a preferred temperature characteristic of the environment may be set to promote a dream sleep state which occurs during REM, though any other use of such transducers to promote the dream state is contemplated. In at least some examples, physiological responses from any one or more of the valence state monitor 200 worn while sleeping and/or the sleep training system 300 may be read instantaneously (and/or subsequently) by a psychoanalyst and/or machine learned model in order to adaptively adjust cues and/or their corresponding levels (e.g., volume).

After one or more sessions, a user may have an interaction with a psychotherapist. In such sessions, the user may describe in detail memories from any dreams recalled during the sessions in the sleep therapy system 300. Feedback may then be incorporated into subsequent cues, which may be uploaded to the valence state monitor 200 and/or the sleep training system 300. Additionally, or alternatively, mantras or other recordings may be adjusted and/or incorporated into the valence state monitor 200 and/or for playback in the sleep training system 300 during subsequent nights.

The Computerized System

Figure 4:
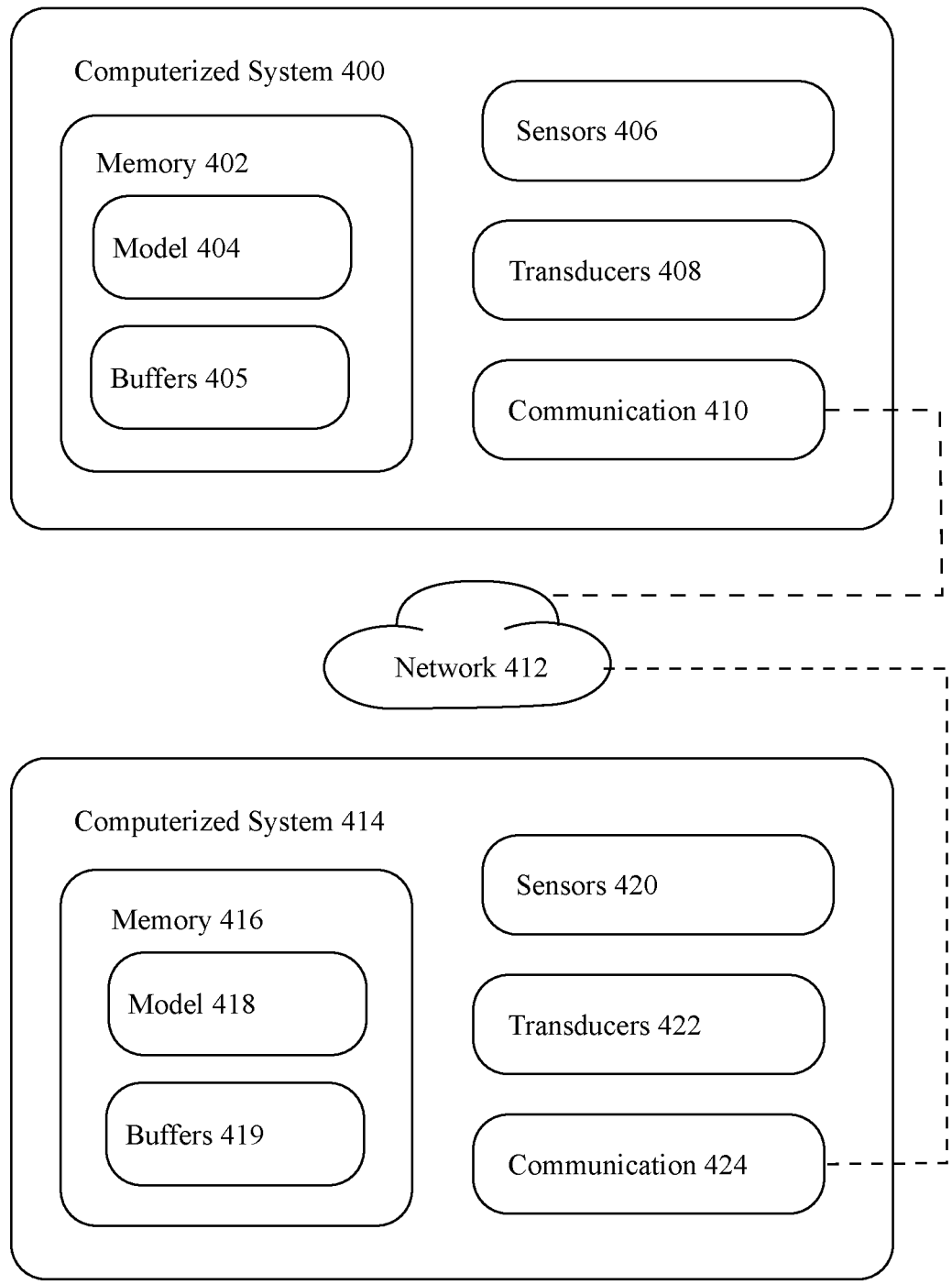
FIG. 4 is an example computerized system capable of performing any one or more of the techniques described herein.

Turning briefly to FIG. 4, a computerized system 400 is depicted as an example computerized system on which the invention may be implemented. For example, such a computerized system 400 may be any one or more of the valence state monitor 200, the sleep training system 300, the computerized footboard 304, the user device 312, the drone 316, and/or any other system capable of implementing the techniques described herein including, without limitation, any one or more systems capable of performing any one or more of the operations described in detail with respect to FIGS. 5 and 6. Although depicted as a single system, such a computerized system 400 may comprise multiple computerized systems and may be either distributed locally, or remotely in various locations. Further, any component need not be local to a single system (e.g., any one or more of memory, processors, components, need no be co-located). The computerized system 400 depicts a computer system comprising memory 402, sensors 406, transducers 408, and a communication component 410. Omitted from FIG. 4 for clarity, such a computerized system 400 may further comprise one or more processors, one or more input/output devices (such as screens, keyboards, mice, buttons, etc., which may comprise input trigger 203), and the like.

The systems and methods described herein can be implemented using one or more computing devices/systems which may or may not be physically or logically separate from each other. The methods may be performed by components arranged as either on-premise hardware, on-premise virtual systems, or hosted-private instances. Additionally, various aspects of the methods described herein may be combined or merged into other functions.

The present invention (or any part(s) or function(s) thereof) may be implemented using hardware, software, firmware, or a combination thereof and may be implemented in one or more computer systems or other processing systems. As illustrated, portions of the techniques described herein may be performed by computerized system 400, whereas other portions may be performed by computerized system 414. As a non-limiting example, the model 418 may be trained on computerized system 414 and subsequently transferred to computerized system 400 as model 404. In some embodiments, the illustrated system elements could be combined into a single hardware device or separated into multiple hardware devices. If multiple hardware devices are used, the hardware devices could be physically located proximate to or remotely from each other. The embodiments of the methods described and illustrated are intended to be illustrative and not to be limiting. For example, some or all of the steps of the methods can be combined, rearranged, and/or omitted in different embodiments.

Such computerized systems 400, 414 may be computers, smartphones, personal digital assistants, smart watches, cloud-based servers (e.g., computer systems accessible over a network programmed to perform particular tasks), and the like.

Memory 402 and memory 416 may comprise, for example, random access memory (RAM), and a secondary memory, etc. Any portions of memory 402 and 416 may comprise transitory and non-transitory computer readable media and/or permanent or rewritable memory, as well as may be volatile and/or non-volatile. Memory 402 and/or memory 416 may be removable or non-removable. Various examples of memory 402, 416 include, but are not limited to, RAM (such as SRAM, DRAM, etc.), ROM (PROM, EPROM, EEPROM), flash memory, hard drives (magnetic, solid state, or the like), floppy drives, optical storage (such as CD-ROMs, DVD-ROMs, etc.), etc.

As illustrated, the memory 402, 416 may comprise any number of buffers 405, 419 which may correspond to the first buffer 208 and/or the second buffer 210. In such examples, buffers 405,419 may be a portion of memory 402,416 and/or another logical unit (flash drive, removable memory, a portion of a hard disk drive, etc.). Memory 402,416 may further comprise one or more operating systems capable of interacting with the one or more processors (not illustrated). In such examples, a portion of memory 402, 416 may be non-transitory computer readable media storing instructions thereon which, when executed by the one or more processors, cause the one or more processors to perform any number of operations. As illustrated with respect to FIG. 4, models 404, 418 may comprise software (instructions) to cause the one or more processors to evaluate sensor data to determine a valence state (e.g., based on the sensor data from a valence state monitor), determine a stage of sleep of a user, and/or train the one or more models 404, 418 as described in detail above. Such models 404, 418 may comprise machine learning models, such as, but not limited to, artificial neural networks, deep learning models, k-means clustering algorithms, logistic and/or linear regression, Bayesian filters, or other signal processing techniques for determining whether a signal (collection of sensor data, which may comprise sensor data over a period of time) is indicative of a valence state.

Any one or more processors (not depicted) in either computerized system 400 and/or 414 may be capable of performing one or more operations based on one or more instructions, or otherwise. Such processors may comprise, for example, Central Processing Units (CPUs), Graphics Processing Units (GPUs), including, without limitation, when used for general purpose graphics programming (GPGPU), field-programmable gate arrays (FPGAs), Application Specific Integrated Circuits (ASICs), and/or any other hardware for performing any number of tasks which may be identified herein.

Any one or more of the computerized systems 400,414 may comprise any number of sensors 406, 420 as described herein. As non-limiting examples, such sensors 406, 420 may include, but are not limited to, microphones, heart rate sensors, EEGs, EKGs, blood pressure sensors, temperature sensors, actigraphy sensors, electrodermal activity sensors, hydration sensors, IMU sensors (accelerometers, gyroscopes, magnetometers), polysomnography sensors, image sensors (cameras, depth cameras, RGB cameras, intensity cameras), infrared sensors, SONAR, RADAR, etc. Any number (subset) of such sensors 406, 420 may be present on either computerized system 400 and/or computerized system 414. Such sensors 406, 420 may record one or more physiological parameters associated with a user for storage (e.g., in memory 406) and or transmission (e.g., over communication component 410).

Any one or more of the computerized systems 400,414 may comprise any number of transducers 408,422 as described herein. Such transducers 408, 422 may comprise, for example, and combination of one or more of air conditioners, fans, lights (including infrared and visible), displays (such as screens), speakers, ultrasonics, liquid atomizers, haptic/vibrational feedback devices, electric shock discharge devices, humidifiers, and the like. Either computerized system 400 or computerized system 414 may comprise different or similar (including the same) combinations of the one or more transducers 408, 422.

Either one or more of the computerized systems 400,414 may comprise one or more communication components 410,424. Such communication components 410,424 may enable either system to communicated with the other which, in some instances, may be over a network, such as network 412. In various examples, such communication components 410,424 may enable communication using wired and/or wireless communications. In any examples, such communication components 410, 424 may use any combination of one or more of internet protocol, hypertext transfer protocol, file transfer protocol, address resolution protocol, internet control message protocol, transmission control protocol, user datagram protocol, and/or any other data communication protocol for transmission of data (token ring, ethernet, and the like).

When using a wireless transmission, such communication component 410,424 may comprise Bluetooth, BTLE, near-field communication (NFC), WiFi, 802.11x, WiMax, LTE, 3G, 4G, 5G, and/or various other wireless communication protocols, components, and/or devices.

The network 412 can include a private network, or a public network (for example the Internet, as described below), or a combination of both. The network includes hardware, software, or a combination of both. The network 412 may be LAN, WAN, or any combination thereof. The network 412 may comprise various nodes to perform various operations on the network, including, but not limited to, servers for routing requests and/or data, as well as cloud-based (remote) servers for data storage and/or manipulation. In at least some examples, such a network 412 may not be necessary. As a non-limiting example, a valence state monitor (such as valence state monitor 200) may communicate directly with another computerized system (e.g., the user device 312, or otherwise) using Bluetooth, NFC, ad-hoc WiFi, or the like.

The systems, modules, and methods described herein can be implemented using any combination of software or hardware elements. The systems, modules, and methods described herein can be implemented using one or more virtual machines operating alone or in combination with one other. Any applicable virtualization solution can be used for encapsulating a physical computing machine platform into a virtual machine that is executed under the control of virtualization software running on a hardware computing platform or host. The virtual machine can have both virtual system hardware and guest operating system software.

One or more embodiments of the invention may be practiced with other computer system configurations, including hand-held devices, microprocessor systems, microprocessor-based or programmable consumer electronics, minicomputers, mainframe computers, etc. The invention may also be practiced in distributed computing environments where tasks are performed by remote processing devices that are linked through a network.

Unless specifically stated otherwise, it may be appreciated that throughout the specification terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors. As used herein, "software" processes may include, for example, software and/or hardware entities that perform work over time, such as tasks, threads, and intelligent agents. Also, each process may refer to multiple processes, for carrying out instructions in sequence or in parallel, continuously or intermittently. The terms "system" and "method" are used herein interchangeably insofar as the system may embody one or more methods and the methods may be considered as a system.

Valence State Monitor

Figure 5:
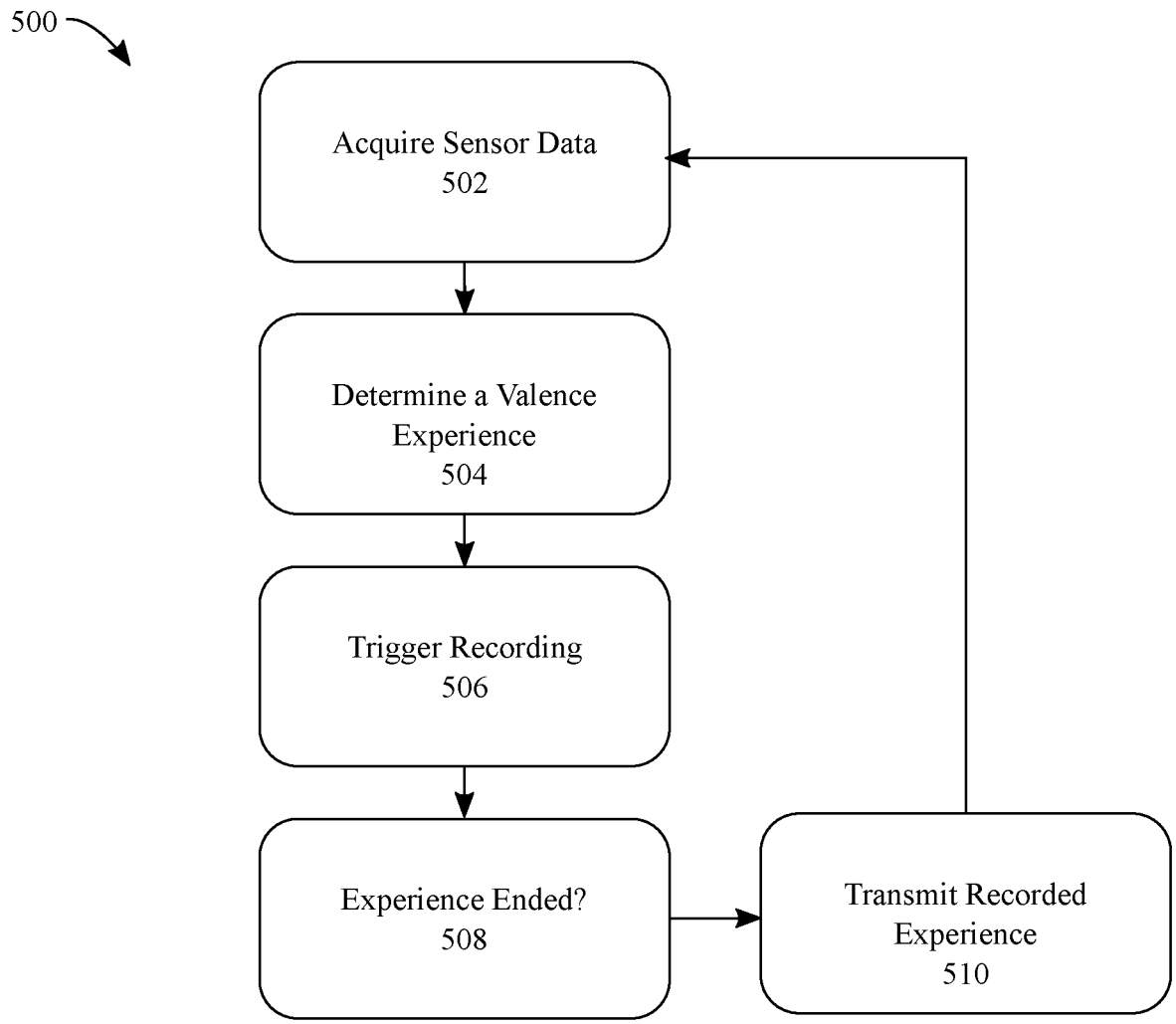
FIG. 5 is an example flow chart depicting an example process flow for performing any one or more of the techniques described in detail herein with respect to determining a valence experience of a user during a waking period of the user.
Figure 6:
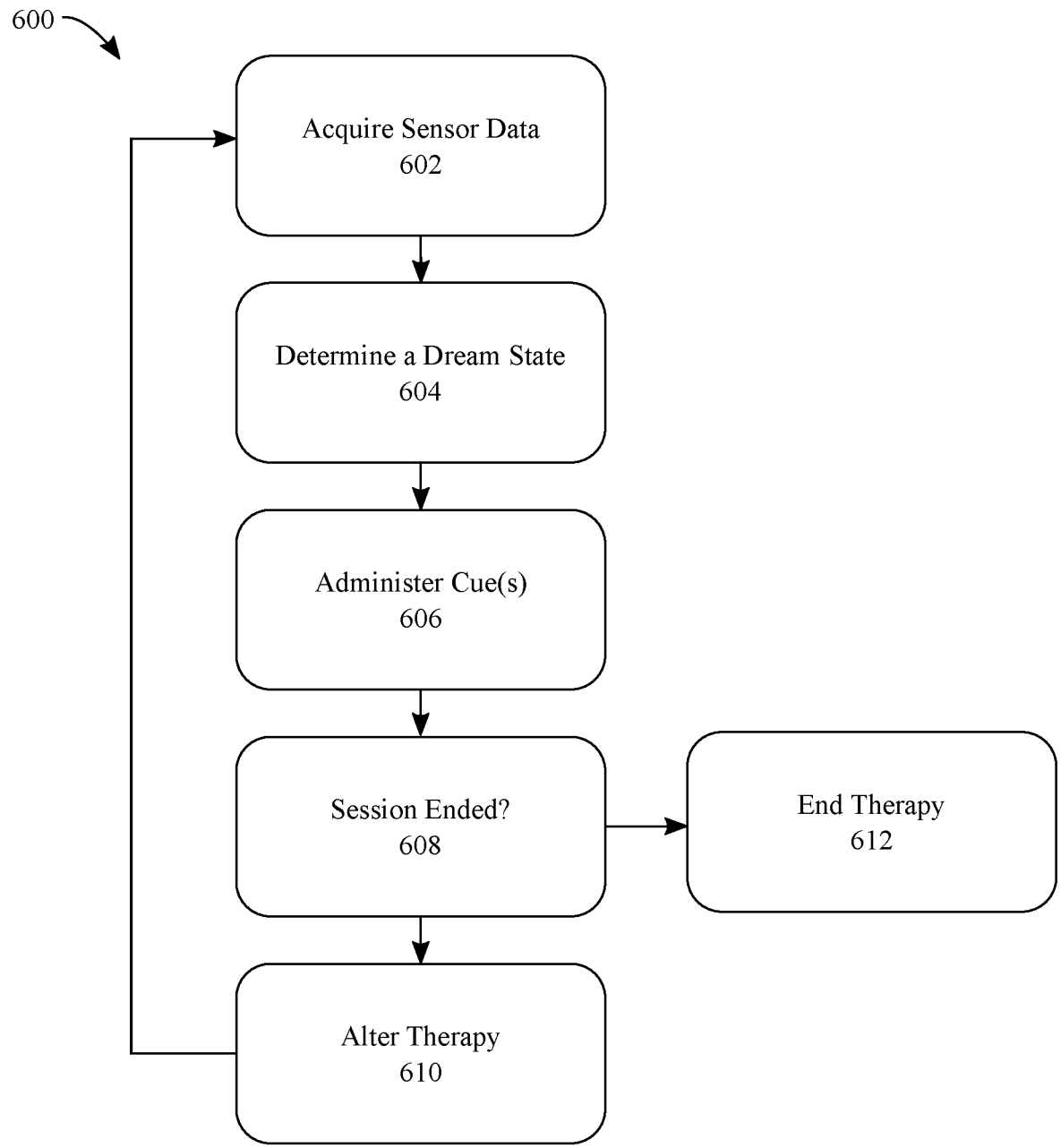
FIG. 6 is an example flow chart depicting an example process flow for performing any one or more of the techniques described herein with respect to determining that a user is in a sleep state and administering one or more cues associated with the valence experience to prime an associative thought during sleep of the valence experience.

FIGS. 5 and 6 represent example flow processes for monitoring a valence state and/or triggering an associated cue during a sleep phase. The processes may be performed by one or more of hardware and/or software, as may be provided by such as system such as the computerized system 400 provided in FIG. 4. When performed as software, the operations depicted (e.g., any one or more of the logical flow boxes) may be performed by one or more processors of a system in response to executing instructions stored on one or more non-transitory computer readable media. Though described as having operations performed in a particular order, such a description is for illustrative purposes and the invention is not meant to be so limiting. Any one or more of the operations presented in FIGS. 5 and 6 may be performed in any order, including substantially simultaneously. Further, any one or more of the operations may be omitted or performed in another order.

FIG. 5 depicts an example flow process for monitoring a valence state, e.g., such as using valence state monitor 200.

At 502, one or more sensors on the valence state monitor worn by a user, or otherwise available to the valence state monitor, may produce sensor data associated with various physiological parameters of the user. As non-limiting examples, such sensor data may comprise heart rate data, EEG data, ECG data, electrodermal activity data, actigraphy data, location data (such as via a GPS), image data (such as from a camera), IMU data, and the like. In at least some examples, such sensor data may be continuously written to a portion of memory associated with the valence state monitor such that the portion of memory consistently has a recording of such physiological data over a given previous amount of time (1 second, 10 seconds, 20 seconds, 30 seconds, 1 minute, and the like), though any time period is contemplated.

At 504, a valence state may be determined (e.g., the user is having a valence experience). As above, such a valence state may be selected by a user and based on a particular outcome the user desired to achieve. As non-limiting examples, such valence states may comprise, for example, overcoming fear or stress, overcoming OCD, overcoming PTSD, overcoming a drug addiction, improving performance of a task, or the like. In at least some examples, physiological responses for each of the aforementioned valence states may differ (e.g., physiological responses for a PTSD event may differ wildly from those associated with enhancing performance of a task). In at least some examples, a user may manually recognize and trigger when the valence event is occurring (e.g., by pressing or otherwise activating an input trigger, such as input trigger 203). In some examples, such a valence state may be determined by one or more machine learned models associated with the valence state monitor. Such machine learned models may ingest a portion of the sensor data and recognize (e.g., by training the model) to recognize the valence event. Such machine learned models may comprise, for example, artificial neural networks, deep learning, various clustering algorithms (such as k-means, DBSCAN, and the like), logistic regression, linear regression, or any other machine learning techniques capable of associating a feature vector (which may comprise a vector of the sensor data and/or a collection of vectors over a period of time) and a particular state (e.g., the valence state). As described above, such machine learning algorithms may use previously collected data associated with the user in a known valence state to train such algorithms.

At 506, based at least in part on determining a valence state has and/or is occurring, a trigger signal may be generated. In response to the trigger signal, subsequently received sensor data may be stored in a separate portion of memory (or otherwise flagged for longer retention in memory). In at least some examples, sensor data stored in the first portion of memory (e.g. that portion of memory associated with 504), may be copied into the second (additional) portion of memory. Such subsequent recording may be for a predefined period of time (30 seconds, 1 min, etc.), or until there is a determination that the user is no longer in the valence state (e.g., a recognition that the various signals have changed and are no longer indicative of the user being in the valence state, as may be determined by the machine learned model of 504).

Additionally in 506, in at least some examples, in response to determining that the user is having a valence experience, the valence state monitor may initiate one or more cues. Such cues may comprise sounds (notes, noises, pre-recordings of the user speaking a mantra, pre-recordings of loved ones telling the user a specific message), lights (infrared, visible, etc.), displays, haptic feedback, electric shocks, and the like. As further described herein, such cues may be adjusted from time to time in accordance with any of the techniques described herein.

At 508, the operations may comprise determining whether the valence experience has ended. As non-limiting examples, such a determination may be based on a predetermined amount of time (whether specified or determined based on previous events), determined based at least in part on a change in sensor data, and/or determined based at least in part on the machine learned model specified above.

At 510, once the experience has ended, the portion of recorded sensor data may be transmitted, via the one or more communication components, to a device (e.g., cloud data storage, another computerized system, etc.). Of course, such data may be later transmitted directly (wired and/or wirelessly), so long as the data remains stored in some portion of the memory associated with the valence state monitor. Additionally, if any cues were being played, such cues may stop at 510. Once data has been transmitted and cues have stopped, flow may proceed back to 502 in order to continue collecting sensor data.

FIG. 6 illustrates an example flow process 600 for priming an associative thought during a dream sleep state associated with a valence state. In at least some examples, priming such an associative thought, the user may be able to alter a valence experience (eliminate, reduce, enhance, etc.) based on experiencing it during a period of sleep.

At 602, sensor data may be acquired from a user during sleep. Such sensor data may be acquired from one or more sensors on a valence state monitor worn during sleep and/or one more additional systems, such as sensors in the footboard/headboard of FIG. 3A, a baseboard 314 or user device 312 as shown in FIG. 3B, or sensors on one or more drone(s) 316 as illustrated in FIG. 3C, though any other number of sensors are contemplated. As above, such sensor data may comprise, for example, heart rate data, electrodermal activity data, EEG data, ECG data, body temperature data, IMU data, actigraphy data, polysomnography data, image data from one or more cameras, sonar data, radar data, blood pressure data, and the like. When such data is obtained from one or more sensors of the valence state monitor (e.g., valence state monitor 108 or 200), the valence state monitor may instantaneously (substantially simultaneously, within technical tolerances) transmit that data to any one or more computerized systems.

At 604, the process may determine that the user has entered a particular sleep phase based at least in part on the physiological data received. As above, such data (such as actigraphy data) may be used to make such a determination (e.g., in accordance with techniques described in, for example, U.S. patent application Ser. No. 14/302,482). In at least some examples, a particular sleep phase is determined. In at least some such examples, such a determination may be made concurrently and/or subsequent to, the operations performed in 606. As a non-limiting example, responses may be measured after administration of the cue in order to determine and/or confirm that the user is in a particular sleep state.

In various examples in which a probing signal is used to determine a sleep phase (e.g., in accordance with the techniques described in the aforementioned patent application), events occurring in the environment may be used as such probing signals for determining a sleep phase. As a non-limiting example, sounds of an air conditioner turning on or high heels clicking down the hallway may be determined (e.g., as a noise rising above a noise threshold) and changes in physiological signals associated with the user can be measured to determine whether or not the user has entered a particular phase of sleep. In such examples, if the user is in either of REM stage sleep or N2 stage sleep, flow may proceed to 606.

At 606, one or more cues may be administered (or otherwise initiated). As described in detail herein, such cues may comprise, for example, a pre-recorded voice (which may be of the user or a loved one) repeating a specific word, mantra, or phrase, noises, sounds, lights (including visible and infrared) which may be in the form of images, patterns, and/or sequences, haptic feedback, electric shocks, temperature control, humidity control, misting of the user with a liquid (such as water), a portion of previously recoded sensor data captured during the valence experience (e.g., one or more sounds captured by a microphone on the valence state monitor), or any combination thereof. In at least some examples, the various cues applied may be based on the particular type of valence experience the user is attempting to alter. As above, in some examples, the cues may be related to a PTSD event (e.g. a particular sound which triggers the event, which may have been recorded by the valence state monitor at the time during waking life that the user experienced a PTSD response), a particular soothing sound for enhancing the user's ability to recall and perform a task, an OCD event, a period associated with intense focus or training, a period of fear, anger, etc., and the like (including additional examples described herein). In at least some examples, such a cue may be associated with one or more advertisements (and/or other media) in which the user was exposed in connection with their buying habits. In at least some examples in which an event occurring in the environment is used to probe the sleep stage, an estimated position to the sound (e.g., a distance to the high heels walking down the hallway), may be used to adjust a volume of the Pavlovian cue to be administered.

During such an operation, the user's memory may be primed for association thought with the valence experience. In such a dream state, the user's mind may be better equipped to alter the user's emotional response, stress, anxiety, etc. and/or otherwise enhance the user's focus to enhance performance of a task. In various examples, such association in the dream state may alter a user's reaction in a similar experience during waking life. In any such examples, a user may experience significantly faster improvement as opposed to the use of extended psychotherapy sessions.

At 608, a determination is made as to whether the session is ended. In some examples, such a determination is based on sensor data indicative of the user no longer being in a particular sleep phase (e.g., no longer in N2 or REM). In such examples, flow may proceed to 610. In other examples, however, (such as where the user has awoken), flow may proceed to 612 in which the therapy session is ended. In at least some examples, any one or more of the transducers may be actuated in order to guide the user back into a particular sleep phase to continue such therapy (e.g., by altering a temperature, playing soothing music, reducing a volume/intensity of the one or more transducers, and the like).

At 610, if the user is still asleep, one or more of the cues may be altered. Such cues may be altered by a therapist from time to time based on interviews with the subject regarding any dreams recalled (e.g., if particular cues are experienced in a dream state, enhance them, if not, change them), how well such sleep training sessions are working (is the frequency of valence experiences increasing, decreasing, is the user's ability to perform a task increasing or decreasing, and the like), etc. In at least some examples, the cues administered in 606 may be altered throughout the course of the night and during sleep such as, for example, by continuously increasing a level associated with such cues up and until a point in which a micro-arousal is induced and or a given amount (e.g., in decibels) below a previously determined transition threshold. In some examples, additional cues and/or sounds may be played in order to cause the user to remain in a particular sleep stage (N2 and/or REM) for as long as possible. In at least some examples, a user's physiological response associated with the administration of the cue may be used to alter the cue. As a non-limiting example, if a cue causes stress, there may be an increase in heartrate variability, whereas a cue which decreases stress may be associated with a decrease in heartrate variability. In such examples, if there the level of heartrate variability is too high (e.g., meets or exceeds a heartrate variability threshold), the cue may be altered (e.g., played at a lower intensity, having different words, more soothing/calming audio, and the like), may be chosen for subsequent administration. In at least some examples, such cue adjustments (performed in 610) may be performed in real-time and/or near real-time.

In any one or more of the examples provided herein, administration of such a cue may be used to align (e.g., synchronize) the one or more data streams. As a non-limiting example, it may be difficult to synchronize IMU data with heartrate data. Additionally, due to the differing frequencies of such measurements, even though initially synchronized, such measurements may not remain aligned (synchronized). In any such example, administration of the cue may be used to demarcate a time (timestamp) used to align (synchronize) multiple data streams, e.g., measurements from the one or more sensors.

In any of the examples herein, a user may be more able to alter (or augment, enhance, etc.) abilities associated with a selected valence state by priming such a memory during a dream phase.

The techniques presented herein improve the performance of a computer. In particular, the techniques enable a user to resolve negative emotional reactions to a valence experience and/or otherwise enhance performance by priming an associative thought of the valence state during a dream state. By priming associative thought in a dream state, a user may be much more quickly able to adapt, alter, and ultimately resolve emotional reactions to such a valence state and/or otherwise improve performance. Such capabilities are not available in existing applications. As such, the systems and techniques presented herein provide technical solutions to the problem of priming an associative thought during a dream state of a valence experience, not previously enabled or otherwise available, thereby improving the performance of a computer/computing system.

While one or more embodiments of the invention have been described, various alterations, additions, permutations and equivalents thereof are included within the scope of the invention.

In the description of embodiments, reference is made to the accompanying drawings that form a part hereof, which show by way of illustration specific embodiments of the claimed subject matter. It is to be understood that other embodiments may be used and that changes or alterations, such as structural changes, may be made. Such embodiments, changes or alterations are not necessarily departures from the scope with respect to the intended claimed subject matter. While the steps herein may be presented in a certain order, in some cases the ordering may be changed so that certain inputs are provided at different times or in a different order without changing the function of the systems and methods described. The disclosed procedures could also be executed in different orders. Additionally, various computations that are herein need not be performed in the order disclosed, and other embodiments using alternative orderings of the computations could be readily implemented. In addition to being reordered, the computations could also be decomposed into sub-computations with the same results.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

In the description and claims, the terms "coupled" and "connected," along with their derivatives, may be used. It should be understood that these terms may be not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

The term "may" is used throughout the disclosure and is not meant to indicate uncertainty regarding the system or techniques described. Throughout the disclosure, use of the word "may" is merely an indication that various limitations and/or features described need not exist in all embodiments or examples, but can exist in at least some examples/ embodiments. When a particular limitation or feature is described in the singular, it is understood that the description is not meant to be so limiting and that any number of such described feature is contemplated.

What is claimed is:

1. A valence monitoring device comprising:
   one or more sensors;
   one or more processors; and
   one or more non-transitory computer readable media having instructions stored thereon which, when executed by the one or more processors cause the one or more processors to perform operations comprising:
      determining that a user wearing the valence monitoring device is in a valence state during the user's waking life, the valence state indicative of the user having a heightened emotional response to an event;
      causing, based at least in part on the user being in the valence state, one or more transducers to produce a first cue;
      receiving, from the one or more sensors at a second time, second sensor data;
      determining, based at least in part on the second sensor data, that the user is in one or more of a rapid eye movement (REM) phase or an $N_2$ phase of sleep;
      causing, based at least in part on determining that the user is in one or more of the REM phase or $N_2$ phase, the one or more transducers to produce the first cue; and
      sending, based at least in part on determining that the user is in one or more of the REM phase or $N_2$ phase, a signal to an additional device, the additional device configured to produce a second cue,
      wherein the additional device comprises one or more of a smartphone, a drone, or a computerized system in a footboard or a headboard of a bed or placed next to the bed.

2. The valence monitoring device of claim 1, wherein determining the user is in the valence state comprises one or more of:
   receiving, from the user, a signal indicative of the user being in the valence state; or determining, based at least in part on first sensor data received from the one or more sensors at a first time prior to the second time, that the user is in the valence state.

3. The valence monitoring device of claim 1,
wherein the one or more sensors comprise one or more of a blood pressure sensor, a heart rate sensor, a electrodermal activity sensor, a temperature sensor, an electroencephaloghy (EEG) sensor, an electrocardiography (EKG) sensor, a sonar sensor, a radar sensor, an actigraphy sensor, an accelerometer, a gyroscope, a magnetometer, a polysomnography sensor, a camera, or a microphone;
wherein the one or more transducers comprise one or more of a speaker, a light emitting diode (LED), an infrared emitter, a screen, a vibrational element, an electric shock discharge device, an air conditioner, or a fan; and
wherein one or more of the first cue or the second cue comprises one or more of a sound, a prerecorded message, a prerecorded word, a portion of first sensor data received from the one or more sensors at a first time prior to the second time, a light pattern, a vibration, or an electric shock.

4. The valence monitoring device of claim 1, wherein the valence state is associated with one or more of:
a drug user experiencing a drug addiction,
an event associated with a post-traumatic stress disorder,
an event associated with an obsessive compulsive disorder,
an event involving task performance ,
an increased period of fear,
an increased period of stress,
an increased period of anxiety,
a period of calm, or
a period of focus.

5. The valence monitoring device of claim 1, wherein determining the user is in the valence state comprises:
receiving, from a psychotherapist, a signal indicative of the user being in the valence state; or
receiving, from the one or more sensors, a signal indicative of the user being in the valence state.

6. The valence monitoring device of claim 1, wherein the instructions, when executed by the one or more processors cause the one or more processors to further perform:
recording, via the one or more sensors, a physiological response of the user to the event while the user is awake.

7. A method comprising:
receiving, at a first time, sensor data from one or more sensors on a valence state monitor worn by a user;
determining, based at least in part on the sensor data, that the user is experiencing, during the user's waking life, a valence state;
causing, based at least in part on the user experiencing the valence state, one or more transducers to produce a first cue;
receiving, at a second time, second sensor data from the one or more sensors;
determining, based at least in part on the second sensor data, that the user is in one or more of a rapid eye movement (REM) sleep phase or an $N_2$ sleep phase;
administering the first cue;
continuously increasing an intensity associated with the first cue;
receiving additional sensor data from the one or more sensors;
determining, based at least in part on the additional sensor data, that the user has experienced a micro-arousal; and
stopping increasing the intensity.

8. The method of claim 7, further comprising:
transmitting a signal to an additional device configured to cause the additional device to administer a second cue, the second cue comprising one or more sounds, light patterns, vibrations, or electric shocks and differing, at least in part, from the first cue.

9. The method of claim 8, wherein the additional device comprises one or more of a smartphone, a drone, or a computerized system in a footboard or headboard of a bed or placed next to the bed.

10. The method of claim 8, wherein the intensity is based at least in part on a distance between the user and the additional device.

11. The method of claim 8, further comprising:
sending the second sensor data to a psychotherapist; and
receiving, from the psychotherapist, an adjustment to one or more of the first cue or the second cue.

12. The method of claim 7, wherein determining that the user is experiencing a valence state comprises one or more of:
receiving input from the user; or
inputting at least a portion of the sensor data into a machine learned model and receiving, from the machine learned model, an indication that the user is in the valence state.

13. The method of claim 7, wherein the one or more sensors comprise one or more of a blood pressure sensor, a heart rate sensor, a electrodermal activity sensor, a temperature sensor, an electroencephaloghy (EEG) sensor, an electrocardiography (EKG) sensor, a sonar sensor, a radar sensor, an actigraphy sensor, an accelerometer, a gyroscope, a magnetometer, a polysomnography sensor, a camera, or a microphone.

14. The method of claim 7, wherein the one or more transducers comprise one or more of a speaker, a light emitting diode (LED), an infrared emitter, a screen, a vibrational element, an electric shock discharge device, an air conditioner, or a fan.

15. The method of claim 7, wherein the valence state is associated with one or more of:
a drug user experiencing a drug addiction,
an event associated with a post-traumatic stress disorder,
an event associated with an obsessive compulsive disorder,
an event involving task performance,
an increased period of fear,
an increased period of stress,
an increased period of anxiety,
a period of calm, or
a period of focus.

16. One or more non-transitory computer readable media having instructions stored thereon which, when executed by one or more processors cause the one or more processors to perform operations comprising:
receiving sensor data from one or more sensors on a device;
determining, based at least in part on the sensor data, that a user wearing the device is experiencing, during the user's waking life, a valence state associated with a valence experience;
storing the sensor data associated with the valence experience;
causing, based at least in part on the user experiencing the valence state, one or more transducers to produce a cue,
wherein the cue comprises one or more of a pre-recorded word, music, a pre-recorded mantra, light, a vibration, or an electric shock;

continuously increasing an intensity associated with the cue;

receiving additional sensor data from the one or more sensors;

determining, based at least in part on the additional sensor data, that the user has experienced a micro-arousal;

stopping increasing the intensity;

determining, based at least in part on the additional sensor data, that the user is in a dream state, the dream state comprising one or more of a rapid eye movement (REM) phase or an N2 phase;

transmitting a signal to one or more additional devices, the one or more additional devices configured to administer an additional cue based on the signal; and producing the additional cue during the dream state.

17. The one or more non-transitory computer readable media of claim 16, wherein one or more of the cue or the additional cue comprises one or more prerecorded messages, a subset of the sensor data, a sound, music, a light pattern, a vibration, or an electric shock.

18. The one or more non-transitory computer readable media of claim 16, wherein the sensors comprise one or more of a blood pressure sensor, a heart rate sensor, a electrodermal activity sensor, a temperature sensor, an electroencephaloghy (EEG) sensor, an electrocardiography (EKG) sensor, a sonar sensor, a radar sensor, an actigraphy sensor, an accelerometer, a gyroscope, a magnetometer, a polysomnography sensor, a camera, or a microphone.

19. The one or more non-transitory computer readable media of claim 16, wherein the transducers comprise one or more of a speaker, a light emitting diode (LED), an infrared emitter, a screen, a vibrational element, an electric shock discharge device, an air conditioner, or a fan.

20. The one or more non-transitory computer readable media of claim 16, wherein determining that the user is experiencing the valence state associated with the valence experience comprises:

inputting at least a portion of the sensor data into a machine learned model; and receiving, from the machine learned model, the determination of whether the user is experiencing the valence state.

21. A method comprising: receiving, at a first time, sensor data from one or more sensors on a valence state monitor worn by a user;

determining, based at least in part on the sensor data, that the user is experiencing, during the user's waking life, a valence state;

causing, based at least in part on the user experiencing the valence state, one or more transducers to produce a first cue;

receiving, at a second time, second sensor data from the one or more sensors;

determining, based at least in part on the second sensor data, that the user is in one or more of a rapid eye movement (REM) sleep phase or an N2 sleep phase; and administering the first cue while the user is in the one or more of the rapid eye movement (REM) sleep phase or the N2 sleep phase.

* * * * *